United States Patent [19]
Boucher, Jr.

[11] Patent Number: 5,292,498
[45] Date of Patent: Mar. 8, 1994

[54] METHOD OF TREATING LUNG DISEASE WITH URIDINE TRIPHOSPHATES

[75] Inventor: Richard C. Boucher, Jr., Chapel Hill, N.C.

[73] Assignee: The University of North Carolina At Chapel Hill, Chapel Hill, N.C.

[21] Appl. No.: 717,747

[22] Filed: Jun. 19, 1991

[51] Int. Cl.$^5$ .................. A61K 31/00; A61L 9/04
[52] U.S. Cl. ........................... 424/45; 424/46; 514/50; 514/51; 514/255
[58] Field of Search ............. 424/45, 46; 514/50, 514/51, 255

[56] References Cited

U.S. PATENT DOCUMENTS

| | | | |
|---|---|---|---|
| 4,501,729 | 2/1985 | Boucher et al. | 514/255 |
| 4,758,553 | 7/1988 | Ogoshi | 514/48 |
| 5,100,647 | 3/1992 | Agus et al. | 424/45 |

OTHER PUBLICATIONS

Rice et al., Br. J. Pharmac., vol. 89, pp. 485–491 (1986).
Cusack et al., Annals N.Y. Acad. Sci., vol. 603, pp. 172–181 (1990).
Endeavors, Research and Graduate Education at The University of North Carolina at Chapel Hill, Fall 1992, vol. X, No. 1.
G. Born and M. Kratzer, J. Physiol. 354, 419–429 (1984).
C. Brown and G. Burnstock, Eur. J. Pharmacol. 69, 81–86 (1981).
G. Burgess et al., Nature 279, 544–546 (1979).
G. Burnstock and C. Kennedy, Circ. Res. 58, No. 3, 319–330 (1986).
G. Burnstock and P. Sneddon, Clinical Science 68, No. 10, 89s–92s (1985).
G. Burnstock, Nature 229, 282–283 (1971).
J. Chapal and M-M Loubatieres-Mariani, Br. J. Pharmac. 73, 105–110 (1981).
N. Cusack and S. Hourani, Annals N.Y. Acad. Sci. 603, 172–181 (G. Dubyak and J. Fedan Eds. 1990).
D. Gallacher, Nature 296, 83–86 (1982).
J. Gordon, Biochem. J. 233, 309–319 (1986).
D. Haussinger et al., Eur. J. Biochem. 167, 65–71 (1987).
M. Maguire and D. Satchell, J. Pharmacol. Exp. Ther. 211, No. 3, 626–631 (1979).
J. Pearson et al., Biochem. J. 214, 273–276 (1983).
W. Rice and F. Singleton, Br. J. Pharmac. 89, 485–491 (1986).

Primary Examiner—Johnnie R. Brown
Assistant Examiner—James O. Wilson
Attorney, Agent, or Firm—Bell, Seltzer, Park & Gibson

[57] ABSTRACT

A method of hydrating mucous secretions in the lungs of a subject in need of such treatment is disclosed. The method comprises administering to the lungs of the subject a uridine triphosphate such as uridine 5'-triphosphate (UTP) or uridine 5'-O-(3-thiotriphosphate) (UTPγS) in an amount effective to hydrate lung mucous secretions. The method is useful for treating patients aflicted with cystic fibrosis. Pharmaceutical formulations and methods of making the same are also disclosed.

26 Claims, 4 Drawing Sheets

METHOD OF TREATING LUNG DISEASE WITH URIDINE TRIPHOSPHATES

This invention was made with Government support under Grants HL34322 and HL42384 from the National Institutes of Health. The Government may have certain rights to this invention.

FIELD OF THE INVENTION

This invention relates to a method of removing retained mucus secretions from the lungs of a patient by administering certain uridine triphosphates to the lungs of the patient.

BACKGROUND OF THE INVENTION

Extracellular adenosine triphosphate has been shown to regulate a variety of biological processes including non-vascular smooth muscle contraction (M. Maguire and D. Satchell, *J. Pharmacol. Exp. Ther.* 211, 626–631 (1979); C. Brown and G. Burnstock, *Eur. J. Pharmacol.* 69, 81–86 (1981)) and vascular tone (G. Burnstock and C. Kennedy, *Circ. Res.* 58, 319–330 (1986); D. Haeussinger et al., *Eur. J. Biochem.* 167, 65–71 (1987)), platelet aggregation (G. Born and M. Kratzer, *J. Physiol. (Lond.)* 354, 419–429 (1984)), neurotransmission (G. Burnstock, *Nature*, 229, 282–283 (1971); G. Burnstock and P. Sneddon, *Clin. Sci.* 68 (Suppl. 10), 89s–92s (1985)), and cellular ion transport (G. Burgess et al., *Nature* 279, 544–546 (1979); D. Galacher, *Nature* 296, 83–86 (1982)) and secretory activities (J. Chapal and M-M. Loubatieres-Mariani, *Br. J. Pharmacol.* 73, 105–110 (1981); J. Pearson et al., *Biochem. J.* 214, 273–276 (1983)). These effects are mediated by specific purinergic receptors which respond to ATP or other nucleotides present in the extracellular millieu (J. Gordon, *Biochem. J.* 233, 309–319 (1986)).

Purinoceptors have been functionally identified in rat pulmonary epithelia in studies of regulation of alveolar Type II surfactant phospholipid secretion (W. Rice and F. Singleton, *Br. J. Pharmacol.* 89, 485–491 (1986)). To our knowledge these receptors have not been reported in human airway epithelial cells. Because ion transport appears to be regulated by purinergic receptor stimulation in other epithelia (Burgess et al., supra (1979); Gallacher, supra (1982)), we investigated several features of the effect of extracellular nucleotides on the ion transport activities of human airway epithelium.

Purinergic receptor regulation of ion transport might have potential therapeutic benefit in lung diseases characterized by abnormalities in epithelial ion transport, e.g., cystic fibrosis. In cystic fibrosis the airway epithelial dysfunction is expressed in part by defective regulation of $Cl^-$ ion transport by secretagogues that regulate the apical cell membrane $Cl^-$ channel by cAMP-dependent or protein kinase C dependent mechanisms (R. Boucher et al., *J. Clin. Invest.* 78, 1245–1252 (1986); R. Boucher et al., *J. Clin. Invest.* 84, 1424–1431 (1989); J. Riordan et al., *Science* 245, 1066–1073 (1989); J. Rommens et al., *Science* 245, 1059–1065 (1989)). Induction of $Cl^-$ secretion by CF airway epithelia in vivo might help liquify the relatively dehydrated, thick airway surface liquid that characterizes this disease. We therefore tested whether nucleotides would bypass regulatory defects in CF airway epithelia and induce $Cl^-$ secretion at rates similar to those of normal airway cells. The present invention is based upon this investigation.

SUMMARY OF THE INVENTION

A method of hydrating mucous secretions in the lungs of a subject in need of such treatment is disclosed. The method comprises administering to the lungs of the subject a compound of Formula I below, or a pharmaceutically acceptable salt thereof (hereinafter referred to as the "active compound"), in an amount effective to hydrate lung mucous secretions:

wherein:

$X_1$, $X_2$, and $X_3$ are each independently either $O^-$ or $S^-$. Preferably, $X_2$ and $X_3$ are $O^-$.

$R_1$ is O, imido, methylene, or dihalomethylene (e.g., dichloromethylene, difluoromethylene). Preferably, $R_1$ is oxygen.

$R_2$ is H or Br. Preferably, $R_2$ is H. Particularly preferred compounds of Formula (I) above are uridine 5'-triphosphate (UTP) and uridine 5'-O-(3-thiotriphosphate) (UTPγS).

The method of the present invention may further comprise the step of concurrently administering amiloride to the subject in an amount effective to inhibit the reabsorption of water from lung mucous secretions.

A second aspect of the present invention is a pharmaceutical formulation containing the active compounds disclosed herein, in an amount effective to hydrate lung mucous secretions, in a pharmaceutically acceptable carrier. The pharmaceutical formulation may further contain amiloride in an amount effective to inhibit the reabsorption of water from lung mucous secretions.

A third aspect of the present invention is the use of the active compounds disclosed herein for the manufacture of a medicament for the therapeutic hydration of mucous secretions in the lungs of a patient in need of such treatment.

DETAILED DESCRIPTION OF THE INVENTION

The method of the present invention may be used to hydrate mucous secretions in the lungs of a subject in need of such treatment for any reason, including (but not limited to) retained secretions arising from airway diseases such as cystic fibrosis, chronic bronchitis, asthma, and bronchiectasis. Hydration of the mucous secretions causes allows them to be more easily transported from the lungs via mucociliary action, and hence facilitates the removal of retained mucous secretions.

The present invention is concerned primarily with the treatment of human subjects, but may also be employed for the treatment of other mammalian subjects, such as dogs and cats, for veterinary purposes.

Compounds illustrative of the compounds of Formula (I) above include: (a) uridine 5′-triphosphate (UTP); (b) uridine 5′-O-(3-thiotriphosphate) (UTPγS); and (c) 5-bromo-uridine 5′-triphosphate (5-BrUTP). These compounds are known or may be made in accordance with known procedures, or variations thereof which will be apparent to those skilled in the art. See generally N. Cusack and S. Hourani, *Annals N.Y. Acad. Sci.* 603, 172–181 (G. Dubyak and J. Fedan Eds. 1990) (titled "Biological Actions of Extracellular ATP"). For example, UTP may be made in the manner described in Kenner et al., *J. Chem. Soc.* 1954, 2288; or Hall and Khorana, *J. Chem. Soc.* 76, 5056 (1954). See Merck Index, Monograph No. 9795 (11th Ed. 1989). UTPγS may be made in the manner described in G. Goody and F. Eckstein, *J. Am. Chem. Soc.* 93, 6252 (1971).

For simplicity, Formula I herein illustrates uridine triphosphate active compounds in the naturally occurring D configuration, but the present invention also encompasses compounds in the L configuration, and mixtures of compounds in the D and L configurations, unless specified otherwise. The naturally occuring D configuration is preferred.

The active compounds disclosed herein may be administered to the lungs of a patient by any suitable means, but are preferably administered by administering an aerosol suspension of respirable particles comprised of the active compound, which the subject inhales. The respirable particles may be liquid or solid. The particles may optionally contain other therapeutic ingredients such as amiloride, with amiloride included in an amount effective to inhibit the reabsorption of water from airway mucous secretions, as described in U.S. Pat. No. 4,501,729 (applicant specifically intends the disclosure of this and all other patent references cited herein be incorporated herein by reference). The term "amiloride" as used herein, includes the pharmaceutically acceptable salts thereof, such as (but not limited to) amiloride hydrochloride. The quantity of amiloride included may be an amount sufficient to achieve dissolved concentrations of amiloride on the airway surfaces of the subject of from about $10^{-7}$ to about $10^{-3}$ Moles/liter, and more preferably from about $10^{-6}$ to about $10^{-4}$ Moles/liter.

The active compounds disclosed herein can be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine.

Particles comprised of active compound for practicing the present invention should include particles of respirable size: that is, particles of a size sufficiently small to pass through the mouth and larynx upon inhalation and into the bronchi and alveoli of the lungs. In general, particles ranging from about 1 to 10 microns in size (more particularly, less than about 5 microns in size) are respirable. Particles of non-respirable size which are included in the aerosol tend to deposit in the throat and be swallowed, and the quantity of non-respirable particles in the aerosol is preferably minimized.

Liquid pharmaceutical compositions of active compound for producing an aerosol may be prepared by combining the active compound with a suitable vehicle, such as sterile pyrogen free water. Other therapeutic compounds such as amiloride may optionally be included.

Solid particulate compositions containing respirable dry particles of micronized active compound may be prepared by grinding dry active compound with a mortar and pestle, and then passing the micronized composition through a 400 mesh screen to break up or separate out large agglomerates. A solid particulate composition comprised of the active compound may optionally contain a dispersant which serves to facilitate the formation of an aerosol. A suitable dispersant is lactose, which may be blended with the active compound in any suitable ratio (e.g., a 1 to 1 ratio by weight). Again, other therapeutic compounds such as amiloride may also be included.

The dosage of active compound will vary depending on the condition being treated and the state of the subject, but generally may be an amount sufficient to achieve dissolved concentrations of active compound on the airway surfaces of the subject of from about $10^{31}$ 7 to about $10^{-3}$ Moles/liter, and more preferably from about $10^{-6}$ to about $3\times10^{-4}$ Moles/liter. Depending upon the solubility of the particular formulation of active compound administered, the daily dose may be divided among one or several unit dose administrations.

Aerosols of liquid particles comprising the active compound may be produced by any suitable means, such as with a pressure-driven aerosol nebulizer or an ultrasonic nebulizer. See U.S. Pat. No. 4,501,729 (applicant specifically intends that the disclosure of this and all other patent references cited herein be incorporated herein by reference).

Aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator comprises a chamber having a rotor mounted therein, which rotor carries a gelatin capsule containing a metered dose of dry particle medicament. In use the capsule is pierced, a patient inhales through the chamber, and the rotor is caused to spin at a speed sufficient to dispense the medicament to thereby form an aerosol of dry particles. A second type of illustrative aerosol generator comprises a pressurized canister containing dry particle medicament in a propellant. The propellant is discharged through a metering valve configured to dispense a metered dose of the dry particle medicament into the atmosphere. The propellant evaporates, leaving an aerosol of dry particle medicament.

The aerosol, whether formed from solid or liquid particles, may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly.

The present invention is explained in greater detail in the Examples which follow. These examples are intended as illustrative of the invention, and are not to be taken as limiting thereof. ATP, UTP, ATPγS, CTP, GTP, ITP, adenylyl-imidodiphosphate (AMPPNP), β,γ-methylene ATP (β,γ-MeATP), ADPβS, ADP, AMP, UDP, 5-BrUTP, UMP, ATPαS and dipyridamole were obtained from Boehringer Mannheim Biochemicals (Indianapolis, Ind.). α,β-methylene ATP (α,β-Me ATP) and amiloride were obtained from Sigma Chemicals (St. Louis, Mo.). 2-methylthio ATP (2MeSATP) was purchased from Research Biochemicals Inc.(Natick, Mass.). Bioelectric properties were measured with confluent monolayers bathed by Ham's F-12 culture solution without hormone supplements (Gibco, Grand Island, N.Y.). The acetoxymethylester of Fura-2 (Fura-2/AM) and the pentapotassium salt Fura-2 were purchased from Molecular Probes (Eugene, Oreg.). To obtain external calibration standards for the dye, the pentapotassium salt Fura-2 was used at 15 μM in solution with 150 mM KCl, 20 mM NaCl, 10 mM 4-(2-hydroxyethyl)-1-piperazine- ethanesulfonic acid (HEPES), and either 5 mM $CaCl_2$ or 2 mM EGTA. For intracellular calcium studies NaCl Ringer solution at 25° C. was employed, containing the following (in millimolar): 150 NaCl, 5 KCl, 5 D glucose, 10 HEPES, 2 $CaCl_2$, 2 $MgCl_2$, adjusted to pH 7.4. For studies using solutions free of calcium, 2 mM EGTA replaced the $CaCl_2$.

EXAMPLE 1

Cell Culture

Freshly excised human nasal epithelium from normal or cystic fibrosis subjects was grown in primary culture in F-12, hormone-supplemented medium in accordance with known procedures. See R. Wu et al., Am. Rev. Respir. Dis. 132, 311–320 (1985). For $[Ca^{2+}]_i$ measurements, cultures were grown on non-fluorescent vitrogen substrates on glass coverslips. Cultures for electrophysiologic studies were grown to confluence on permeable collagen matrix supports (CMS), allowing addition of agonists to the basolateral or apical surface of the epithelial sheet.

EXAMPLE 2

Bioelectric Studies

Confluent monolayers of primary human nasal epithelium were mounted in modified Ussing chambers in accordance with known procedures. See, e.g., R. Boucher et al., *J. Physiol.* (*Lond.*) 405, 77–103 (1988); M. Knowles et al., *Science* 221, 1067–1070 (1983). The studies described below were performed under short circuit current conditions at 37° C., and in some studies, amiloride was added to the apical bath ($10^{-4}$M) to block transepithelial sodium transport. Changes in transepithelial potential difference ($V_t$), resistance ($R_t$) and short circuit current ($I_{sc}$) were measured in response to addition of various nucleotides. Each cultured preparation was exposed to only one concentration of an agonist on either the basolateral or apical surface to avoid the tachyphylaxis observed in preliminary cumulative dose response studies. To construct concentration-effect relationships of responses to nucleotides, it was assumed that the same maximum response to an agonist could be induced from each tissue culture preparation from the same individual.

EXAMPLE 3

Measurements of Intracellular Calcium

Primary human nasal epithelial cells grown to confluence on vitrogen coated coverslips were loaded with a final concentration of 3 μM Fura-2/AM at 37° C. for 30 minutes. The cells were then washed in NaCl Ringer and mounted in a chamber for measurements of fluorescence. To reduce the rate of leakage of Fura-2 from the cell into the extracellular space and avoid time-dependent compartmentalization of the probe, all measurements of $[Ca^{2+}]_i$ were performed at 25° C. At this temperature, no vesicular bright spots indicative of compartmentalization of the probe were observed.

Measurements of $[Ca^{2+}]_i$ in single human nasal epithelial cells were obtained with a modular microspectrofluorimeter (SPEX Industries, Inc., Edison, N.J.) attached to a Zeiss Axiovert IM 35 microscope. The system was equipped with a xenon lamp, beam splitter, two monochromators and a rotating chopper mirror that permitted excitation of cell fluorescence at alternating wavelengths of 340 and 380 nm (emission $\geq 450$ nm). The fluorescent signal from a single cell was measured with a photometer equipped with a pinhole (spot diameter of 3-5 $\mu$m) that excluded signals from adjacent cells.

After agonist was added, the fluorescent signal was quenched by a NaCl ringer solution containing $1.5 \times 10^{-4}$M digitonin and $10^{-3}$M MnCl$_2$. The remaining signal at each excitation wavelength, equivalent to the background fluorescence in non loaded cells, was subtracted from data from Fura-2/AM loaded cells before the ratio (340 nm/380 nm) was taken. The 340 nm/380 nm ratio was converted to an actual $[Ca^{2+}]_i$ measurement by using the external calibration standards and the formula derived by G. Grynkiewicz et al., *J. Biol. Chem.* 260, 3440-3450 (1985), used with dual wavelength measurements: $[Ca^{2+}]_i = K [(R_x - R_o)/(R_s - R_x)]$, with $R_o$ and $R_s$ representing the ratios at 0 Ca$^{2+}$ and saturating Ca$^{2+}$, respectively. $R_x$ represents the experimental ratio. K is $K_d(F_o/F_s)$, with $K_d = 1.57 \times 10^{-7}$M at 25° C. as the effective dissociation constant for Fura-2, and $F_o$ and $F_s$ represent the fluorescence intensities at 380 nm with zero and saturating Ca$^{2+}$, respectively.

EXAMPLE 4

Normal Human Nasal Epithelium—Ion Transport

The effects of extracellular ATP on normal human nasal epithelium were investigated employing bioelectric measurements of ion transport activity when the nucleotide was applied to either the apical or basolateral membrane. ATP rapidly stimulated an increase in $I_{sc}$ when applied to either surface (data not shown). In general, the change in $I_{sc}$ induced by application of ATP to the apical or the basolateral side returned to baseline or below within 5 minutes after addition of agonist. Oscillations in $I_{sc}$ following ATP were frequently observed. Apical pretreatment with amiloride ($10^{-4}$M) removes active Na$^+$ absorption as a component of the $I_{sc}$ so that the residual $I_{sc}$ reflects a Cl$^-$ secretory current (R. Boucher et al., *J. Clin. Invest.* 78, 1245-1252 (1986); N. Willumsen et al., *Am. J. Physiol.* 256, C1033-C1044 (1989)).

A typical Cl$^-$ secretory response of human nasal epithelium was found when ATP is applied to amiloride-pretreated tissues (data not shown). Following the initial peak, the ATP induced increase in $I_{sc}$ after basolateral addition to amiloride-pretreated tissues returned to baseline within 5 minutes. In contrast, most tissues treated with ATP on the apical surface following amiloride pretreatment exhibited prolonged (>10 minutes) increases in $I_{sc}$ above baseline levels.

A concentration-effect relationship was found when ATP was applied to normal human nasal epithelium under basal conditions (data not shown). Comparisons were made between responses of tissues from different donors based on the peak change in $I_{sc}$ following ATP application. The curve describes the mean peak change in $I_{sc}$ in response to log increasing concentrations of ATP applied to the apical or basolateral surface. The effectiveness of the nucleotide is approximately equal when applied to the apical or basolateral surface between $10^{-7}$ and $10^{-4}$M. A large increase in $I_{sc}$ is seen with $10^{-3}$M ATP applied to the basolateral membrane that is not seen with apical application.

Concentration-effect relationships were also found for ATP applied to the apical or basolateral membrane of amiloride-pretreated tissues (data not shown). Again, the nucleotide's effect on ion transport was examined as the mean peak change in $I_{sc}$ after ATP application. The change in ion transport induced by ATP in amiloride-pretreated tissues is routinely smaller than that observed in tissues in the basal state. The potency and effectiveness of ATP in amiloride-treated tissues are similar whether applied to the apical or basolateral membrane and the log concentration-effect curves are sigmoidal in character, with EC$_{50}$ values of approximately $1-2 \times 10^{-5}$M.

The purinergic receptor subtype(s) linked to regulation of ion transport of human nasal epithelium were characterized by obtaining concentration-effect relationships for a variety of purine and pyrimidine agonists in preparations derived from normal and CF patients. We characterized receptor subtype(s) on the basolateral surface by measuring nucleotide effect on basal Na$^+$ transport rates. Because therapies designed to induce Cl$^-$ secretion might best be delivered by the aerosol route, receptor subtype characterization on the apical barrier was performed in the presence of amiloride. The effect of extracellular nucleotides on ion transport is reported as the percent change in $I_{sc}$ from control values when applied to the basolateral or apical surface of the culture. Basal pre-agonist currents were similar for tissues in each concentration group.

Under the culture conditions employed in these studies, the P$_1$ receptor agonist adenosine, following preincubation of tissues with dipyridamole [$10^{-6}$M] to block adenosine uptake, induced only small and variable changes in $I_{sc}$ compared to ATP (compare with FIGS. 1 and 2, below). Addition of adenosine to the apical surface of amiloride-pretreated human nasal epithelium at $10^{-5}$M (n=7) or $10^{-4}$M (n=8) induced an increase of $10 \pm 7$ or $10 \pm 6$ percent, respectively, whereas addition of the same doses to the basolateral barrier (n=8, each dose) raised $I_{sc}$ by less than 5 percent. These findings suggest that the activation of P$_1$ receptors contributes little to the measured effects of extracellularly applied ATP on ion transport. Therefore, we focused on agonists that interact with P$_2$ receptors in the regulation of ion transport and $[Ca^{2+}]_i$ mobilization in human nasal epithelium.

Figure 1:
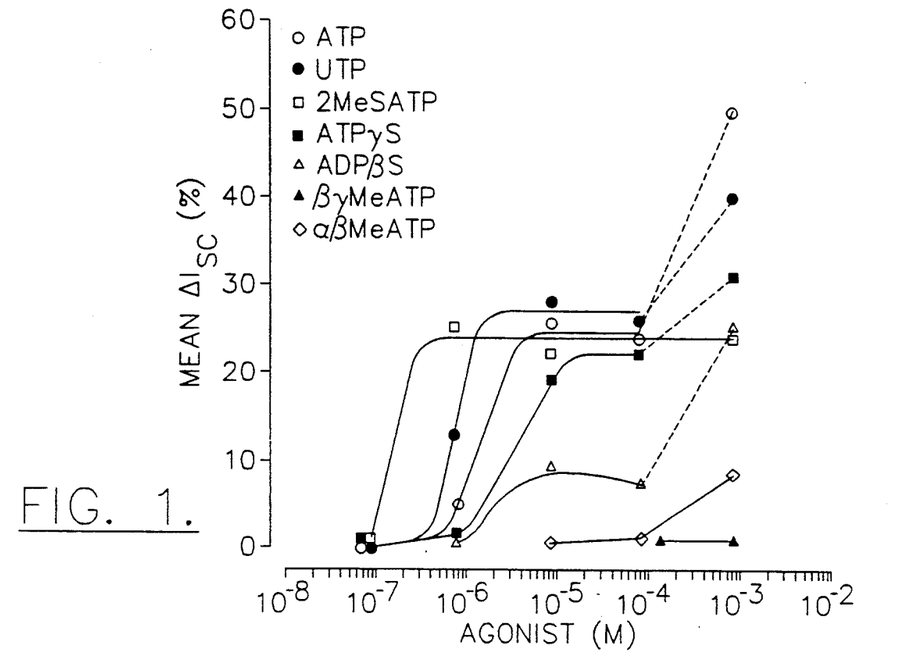
FIG. 1 shows the log concentration-effect curves (percent change in $I_{sc}$ from basal levels) of nucleotides applied to the basolateral surface of normal human nasal epithelium. s.e. of each data point is $\leq 15\%$ of the normalized maximum response.

FIG. 1 illustrates the concentration-effect relationships of agonists applied to the basolateral surface of airway epithelium. In FIG. 1, mean basal $I_{sc}$ in each set of experiments were (in $\mu$A cm$^{-2}$): ATP (○), $69 \pm 5$, range 55-80, n=5 (n=3-11 at each agonist concentration); UTP (●), $66 \pm 9$, range 21-158, n=9 (n=3-23); 2MeSATp (□), $48 \pm 6$, range 35-65, n=6 (n=3-17); ATP$\gamma$S (■), $47 \pm 8$, range 28-72, n=3 (n=3); ADP$\beta$S (△), $49 \pm 6$, range, 36-65, n=3 (n=3); $\alpha\beta$MeATP (◊), $51 \pm 12$, range 28-66, n=3 (n=3); $\beta\gamma$MeATP (▲), $79 \pm 21$, range 59-100, n=3 (n=3). Compared to the concentration-effect curve of ATP, agonists that stimulate $P_{2x}$ receptors ($\alpha\beta$MeATP and $\beta\gamma$MeATP) induced little change in ion transport rates. The observed rank order of potency for agonists that significantly increased $I_{sc}$ was 2MeSATP>UTP≧ATP>ATP$\gamma$-S>ADP>ADP$\beta$S. At concentrations of ATP, UTP, ATP$\gamma$S or ADP$\beta$S between $10^{-7}$ and $10^{-4}$M, the relationship between log agonist concentration and observed responses was a curve of sigmoidal character. The concentration-effect curve of these agonists was biphasic in character when the effect on $I_{sc}$ of $10^{-3}$M drug was considered.

Figure 2:
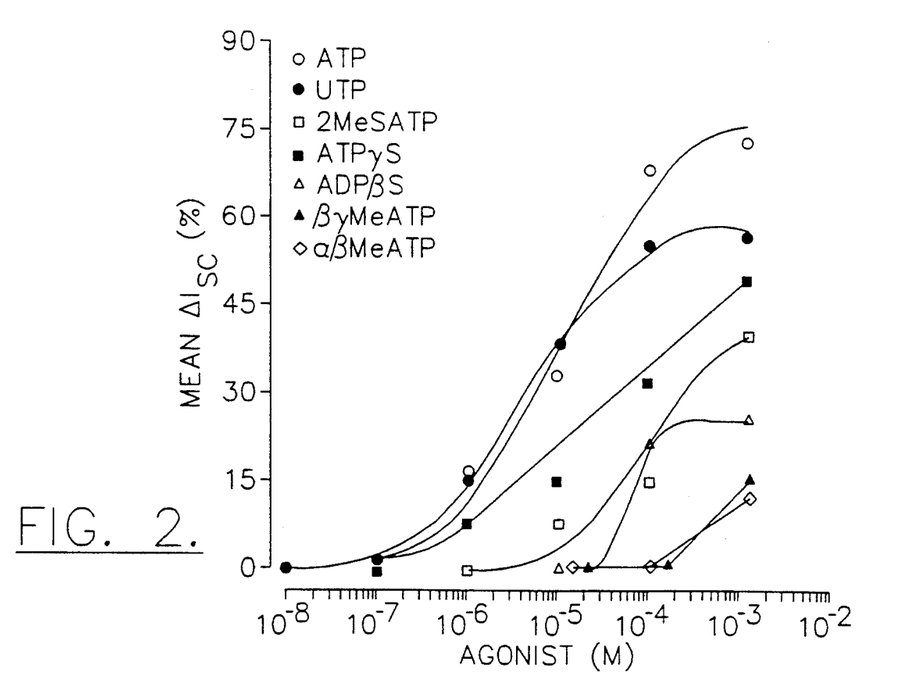
FIG. 2 shows the log concentration-effect curves (percent change in $I_{sc}$ from basal levels) of nucleotides applied to the apical surface of human nasal epithelium pretreated with amiloride ($10^{-4}$M). s.e. of each data point is $\leq 13\%$ of the normalized maximum resonse.

The concentration-effect relationships for nucleotides added to the apical surface of amiloride-pretreated tissues are shown in FIG. 2. In FIG. 2, mean post amiloride $I_{sc}$ in each set of experiments were (in $\mu$A cm$^{-2}$): ATP (○), 13±1, range 9–16, n=8 (n=3–11 at each agonist concentration); UTP (●), 12±1, range 11–15, n=5 (n=3–17); ATP$\gamma$S (■), 12±1, range 8–15, n=3 (n=3); 2MeSATP (□), 16±2, range 12–21, n=3 (n=3–7); ADP$\beta$S (△), 15±1, range 13–16, n=3 (n=3); $\beta\gamma$MeATP (▲), 14±0, range 8–19, n=3 (n=3); $\alpha\beta$-MeATP (◊), 11±0, range 7–14, n=3 (n=3). Compounds reported to be effective $P_{2x}$ receptor agonists stimulated little change in ion transport by airway epithelium. Those reported to be effective $P_{2y}$ or UTP sensitive receptor agonists stimulated Cl$^-$ secretion with the following rank order of potency: ATP≧UTP->ATP$\gamma$S>ADP>2MeSATP>ADP$\beta$S.

EXAMPLE 5

Normal Human Nasal Epithelium—Intracellular Calcium

Based on studies in other epithelia indicating that regulation of [Ca$^{2+}$]$_i$ by purinergic receptors initiates changes in ion transport rates (G. Kimmich and J. Randles, *Am. J. Physiol.* 243, C116–C123 (1982)), we asked whether ATP regulated [Ca$^{2+}$]$_i$ in single human nasal epithelial cells using intracellular Ca$^{2+}$ sensitive fluorescent dye. Extracellular application of ATP induced an immediate increase in [Ca$^{2+}$]$_i$ levels that decreased over 1 to 2 minutes to a prolonged plateau (data not shown). Exposure to ATP in Ca$^{2+}$-free medium resulted in an initial sharp increase in [Ca$^{2+}$]$_i$ which returned to baseline over a two minute period with no plateau phase observed (data not shown). Return of the cells to a Ca$^{2+}$-containing solution resulted in restoration of the plateau phase in the Ca$^{2+}$ response to ATP.

Figure 3A:
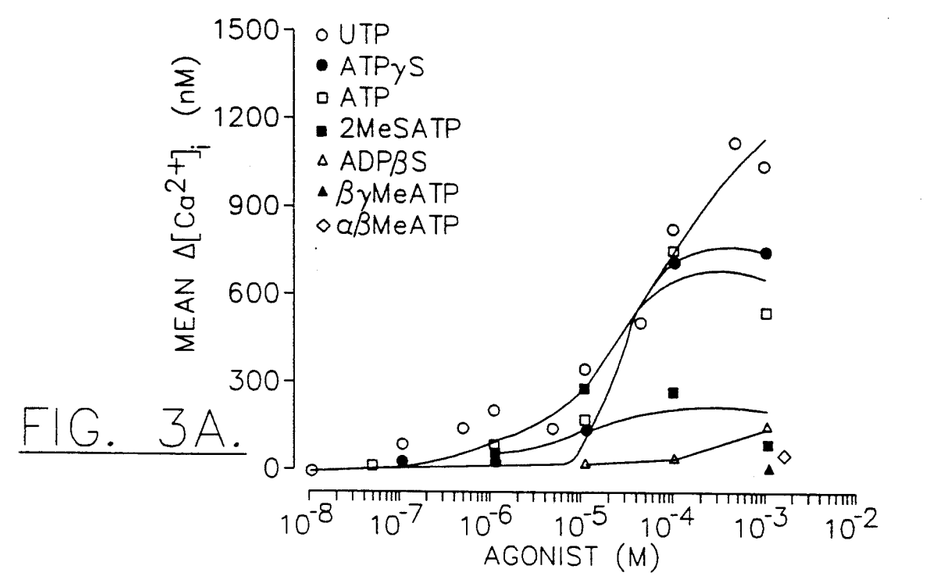
FIG. 3A shows, in log concentration-effect on $[CA^{2+}]_i$, a comparison of agonists which bind $P_{2x}$, $P_{2y}$ or UTP sensitive receptors, mean basal $[CA^{2+}]$, in each set of experiments were (in nM): UTP (○), 81±8, range 48-113, n=5 (n=3-6); ATPτS (●), 116±11, range 85-151, n=4 (n=3-6); ATP (□), 61±3, range 51-70, n=8 (n=3-8 at each agonist concentration); 2MeSATP (■), 123±19 range 95-180, n=3 (n=3); ADPβS (Δ), 91±17, range 74–107, n=3 (n=3); αβMeATP (◊), 82±16, range 50–99, n=3 (n=3); βγMeATP (▲), 68±4, range 61–74, n=3 (n=3).
Figure 3B:
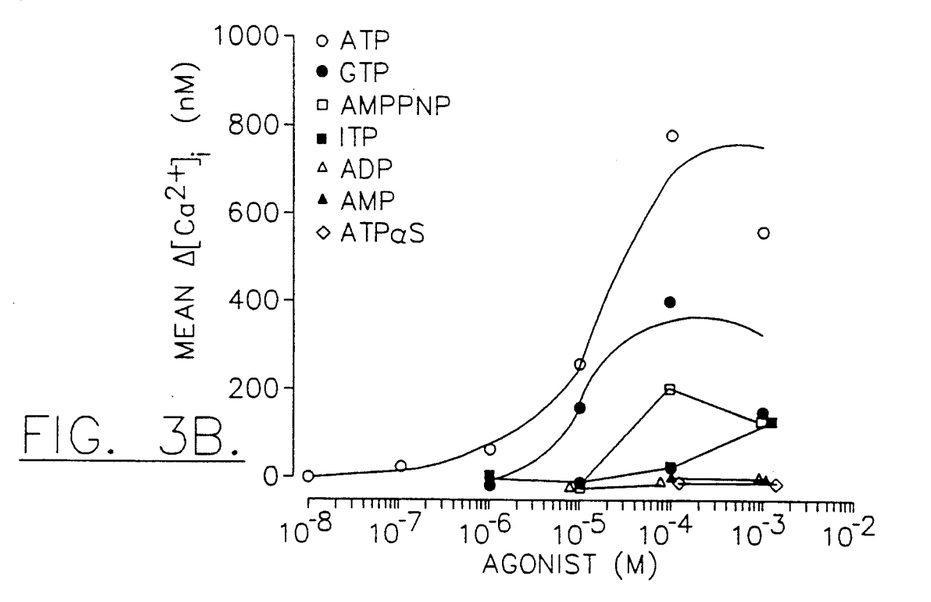
FIG. 3B shows, in log-concentration effect on $[Ca^{2+}]_i$, a comparison of other purine agonists with response stimulated by ATP (○), mean basal $[Ca^{2+}]$, in each set of experiments were (nM): GTP (●), 117±13, range 92–153, n=3 (n=3; AMPPNP (□), 137±50, range 74–235, n=3 (n=3; ITP (■), 103±10, range 85–121, n=3 (n=3); ADP (Δ), 94±16, range 75–127, n=3 (n=2–3); AMP (▲), 111±28, range 69–189, n=3 (n−3); ATPαS (◊), 89±2, range 87–91, n−1 (n=2).
Figure 3C:
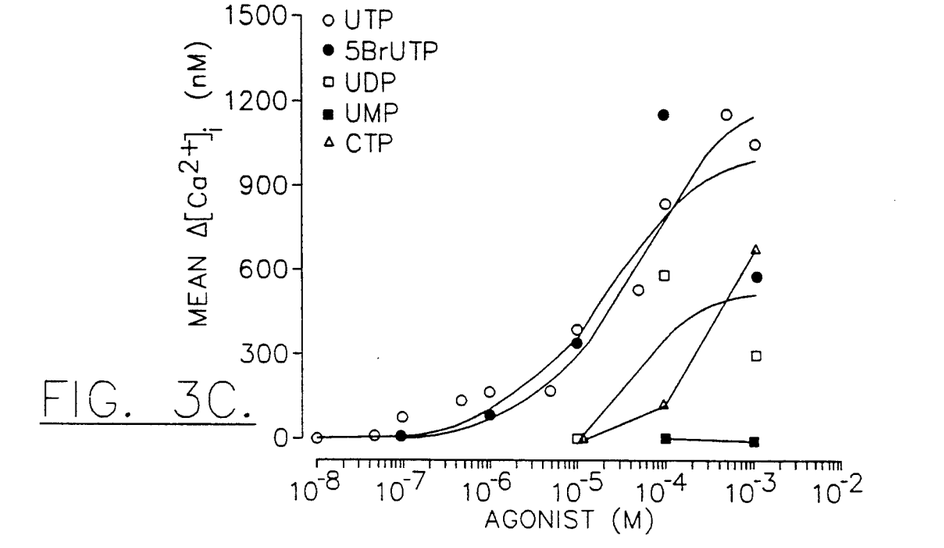
FIG. 3C shows, in log-concentration effect on $[Ca^{2+}]_i$, a comparison of UTP (○) with other pyrimide agonists, mean basal $[Ca^{2+}]$, (in nM): 5BrUTP (●), 110±13, range 82–152, n=3 (n=2–3); UDP (□), 89±2, range 84–92, n=3 (n=3); CTP (Δ), 83±10, range 69–102, n=3 (n=3); UMP (■), 78±14, range 64–91, n=2 (n=2).

To investigate whether changes in [Ca$^{2+}$]$_i$ might be related to regulation of ion transport, receptor characterization was performed by measuring changes in [Ca$^{2+}$]$_i$ in response to a number of nucleotide drugs. Concentration-effect curves for agonists active at $P_{2x}$, $P_{2y}$ subtype or UTP sensitive receptors and other purine or pyrimidine receptor agonists were generated, measuring mean change in [Ca$^{2+}$]$_i$ in response to agonist concentration. Data are shown in FIG. 3, which gives log concentration-effect relationships of purinergic and pyrimidinergic compounds on [Ca$^{2+}$]$_i$ (mean change in [Ca$^{2+}$]$_i$ over basal levels). FIG. 3A shows a comparison of agonists which bind $P_{2x}$, $P_{2y}$ or UTP sensitive receptors, mean basal [Ca$^{2+}$]$_i$ in each set of experiments were (in nM): UTP (○), 81±8, range 48–113, n=5 (n=3–6); ATP$\gamma$S (●), 116±11, range 85–151, n=4 (n=3–6); ATP (□), 61±3, range 51–70, n=8 (n=3–8 at each agonist concentration); 2MeSATP (■), 123±19 range 95–180, n=3 (n=3); ADP$\beta$S (△), 91±17, range 74–107, n=3 (n=3); $\alpha\beta$MeATP (◊), 82±16, range 50–99, n=3 (n=3); $\beta\gamma$MeATP (▲), 68±4, range 61–74, n=3 (n=3). FIG. 3B shows a comparison of other purine agonists with response stimulated by ATP (○), mean basal [Ca$^{2+}$]$_i$ in each set of experiments were (nM): GTP (●), 117±13, range 92–153, n=3 (n=3); AMPPNP (□), 137±50, range 74–235, n=3 (n=3); ITP (■), 103±10, range 85–121, n=3 (n=3); ADP (△), 94±16, range 75–127, n=3 (n=2–3); AMP (▲), 111±28, range 69–189, n=3 (n=3); ATP$\alpha$S (◊), 89±2, range 87–91, n=1 (n=2). FIG. 3C shows a comparison of UTP (○) with other pyrimidine agonists, mean basal [Ca$^{2+}$]$_i$ (in nM): 5BrUTP (●), 110±13, range 82–152, n=3 (n=2–3); UDP (□), 89±2, range 84–92, n=3 (n=3); CTP (△), 83±10, range 69–102, n=3 (n=3); UMP (■), 78±14, range 64–91, n=2 (n=2).

ATP, UTP and ATP$\gamma$S were the most effective agonists. Classical $P_{2x}$ ($\alpha\beta$MeATP and $\beta\gamma$MeATP) and $P_{2y}$ (2MeSATP and ADP$\beta$S) receptor agonists had little effect (FIG. 3A) as did other analogs of ATP and ADP (FIG. 3B). 5BrUTP was essentially as effective as UTP for stimulation of Ca$^{2+}$ mobilization (FIG. 3C).

EXAMPLE 6

Cystic Fibrosis Nasal Epithelium

Availability of Cystic Fibrosis (CF) tissues is limited, and our investigation of effects of nucleotides was restricted to examining regulation of Cl$^-$ secretion rates and [Ca$^{2+}$]$_i$ levels by ATP and UTP. Only small changes in Cl$^-$ secretion (amiloride-resistant $I_{sc}$) were observed in CF tissues following basolateral addition of ATP [14±3 maximum mean % change in $I_{sc}$ (n=6)] compared with normal tissues [51±8 maximum mean % change in $I_{sc}$ (n=6)]. Apical administration of ATP following blockade of Na+ absorption with amiloride resulted in two distinct patterns of response in tissues from CF subjects. Data are given in FIGS. 4A, 4B, 4C and 5.

Figure 4A:
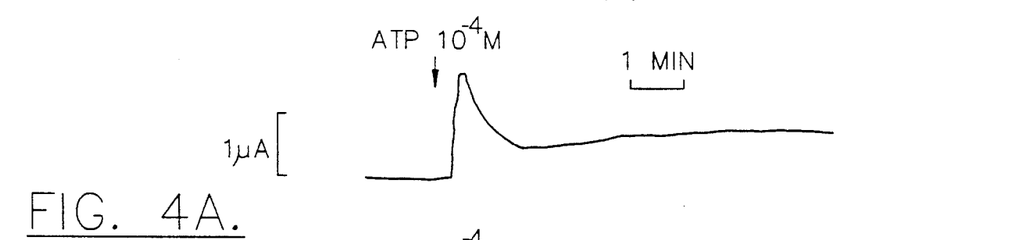
FIG. 4A provides a bioelectric tracing of the effect on $I_{sc}$ of extracellular ATP ($10^{-4}$M) applied to the apical surface of amiloride-pretreated ($10^{-4}$M) CF human nasal epithelium, showing Cl$^-$ secretion in response to ATP (post-amiloride $I_{sc}=13$ $\mu$A.cm$^{-2}$).
Figure 4B:
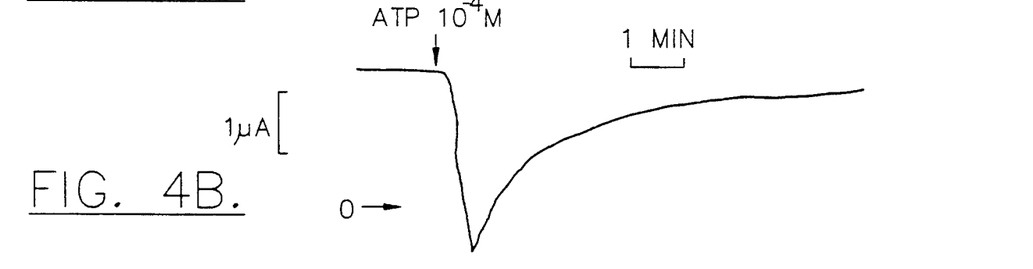
FIG. 4B is a bioelectric tracing like FIG. 4A showing the $I_{sc}$ response to ATP ($10^{-4}$M) of opposite polarity (post-amiloride $I_{sc}=19$ $\mu$A.cm$^{-2}$).
Figure 4C:
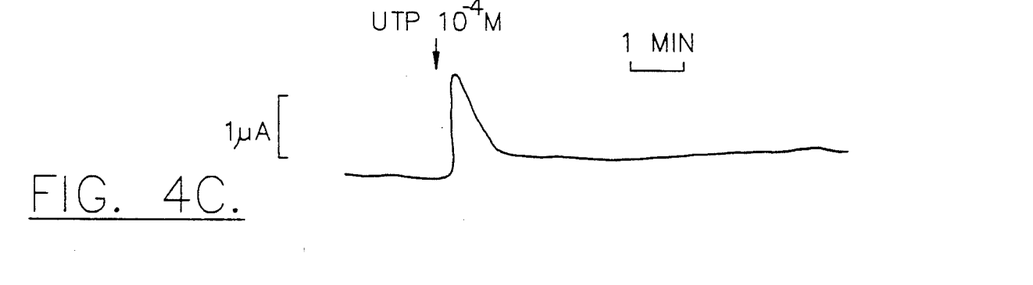
FIG. 4C is a bioelectric tracing like FIG. 4A showing the Cl$^-$ secretory response to UTP ($10^{-6}$M) (post-amiloride $I_{sc}=5$ $\mu$A.cm$^{-2}$).

FIGS. 4A, 4B, 4C provides representative bioelectric tracings of effect on $I_{sc}$ of extracellular ATP ($10^{-4}$M) or UTP ($10^{-4}$M) applied to the apical surface of amiloride-pretreated ($10^{-4}$M) CF human nasal epithelium. (A) Cl$^-$ secretion in response to ATP (post-amiloride $I_{sc}$=13 $\mu$A.cm$^{-2}$). (B) $I_{sc}$ response to ATP of opposite polarity (post-amiloride $I_{sc}$=19 $\mu$A.cm$^{-2}$) (C) Cl$^-$ secretory response to UTP (post-amiloride $I_{sc}$=5 $\mu$A.cm$^{-2}$).

Figure 5:
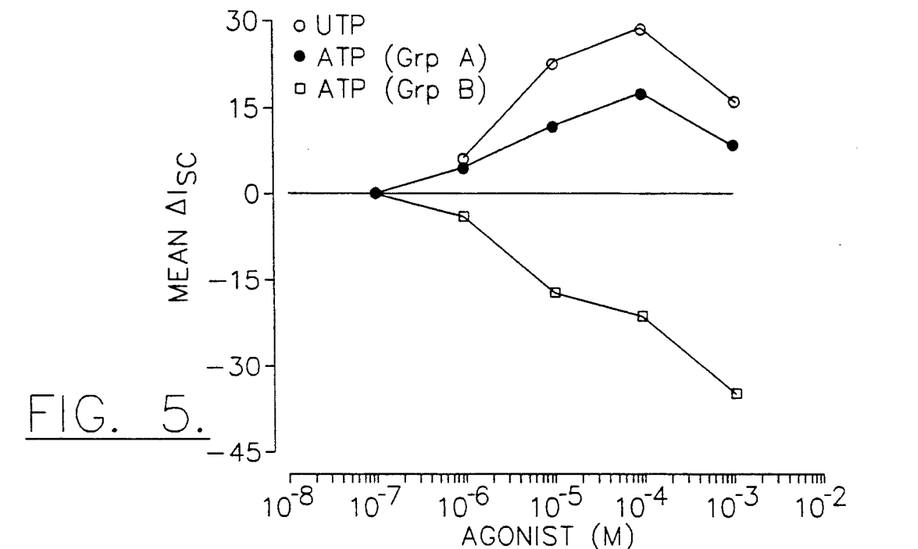
FIG. 5 shows the log concentration-effect curves for changes in $I_{sc}$ from basal levels when ATP or UTP are applied to the apical surface of amiloride-pretreated CF tissues. s.e. of each data point is $\leq 13\%$ of the normalized maximum response.

FIG. 5 shows log concentration-effect curves for changes in $I_{sc}$ from basal levels when ATP or UTP are applied to the apical surface of amiloride-pretreated ($10^{-4}$M) CF tissues. Mean post amiloride $I_{sc}$ in each set of experiments were (in $\mu$A.cm$^{-2}$): ATP [Grp A (●), Grp B (□)], 13±1, range 3–31, n=4 (n=4–13 at each agonist concentration); UTP (○), 12±2, range 8–14, n=3 (n=3). s.e. of each data point is ≦13% of the normalized maximum response.

Most tissues exhibited an increase in $I_{sc}$ over basal levels after ATP (FIG. 4A), suggesting stimulation of Cl$^-$ secretion. However, approximately 30% of CF tissues tested responded with a change to opposite polarity of $I_{sc}$ following ATP (FIG. 4B), suggesting a secretion dominated by cations in these preparations (Bean and D. Friel, *In: Ion Channels*, Vol. 2, 169–203 (T. Narahashi, Ed. 1990)). UTP applied to the apical surface routinely stimulated increases in Cl$^-$ secretion in CF tissues (FIG. 4C). Mean peak change in $I_{sc}$ from post-amiloride basal levels in response to ATP or UTP application was measured in individual CF tissues to obtain the concentration-effect relationships illustrated in FIG. 5.

Figure 6:
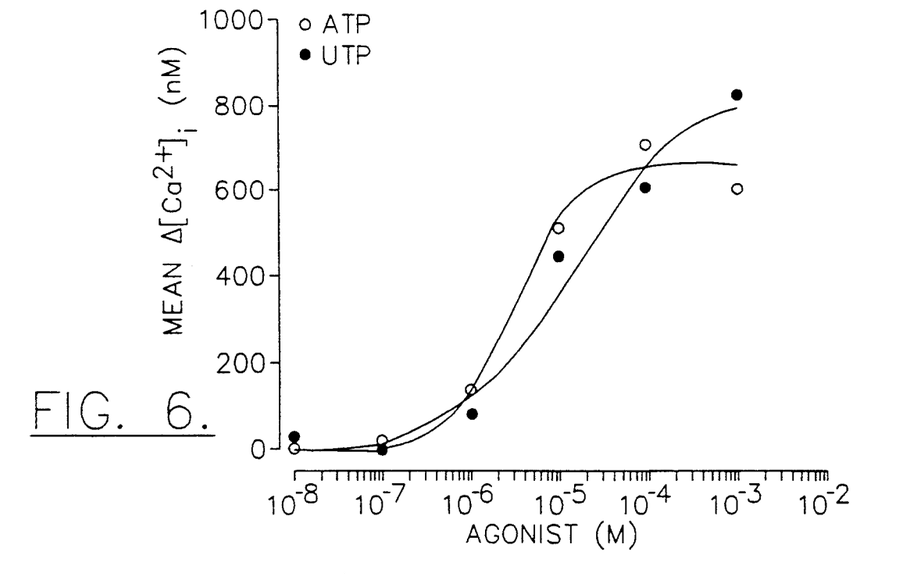
FIG. 6 shows the log concentration-effect relationships of the effect of ATP and UTP on $[Ca^{2+}]_i$ (change from basal levels) in single CF nasal epithelial cells. s.e. of each data point is $\leq 8\%$ of the normalized maximum response.

Increases in $[Ca^{2+}]_i$ in CF tissues were also observed after addition of ATP or UTP. Data are given in FIG. 6 which shows the log concentration-effect relationships of the effect of ATP and UTP on $[Ca^{2+}]_i$ (change from basal levels) in single CF nasal epithelial cells. Mean basal $[Ca^{2+}]_i$ (in nM): ATP (○), 65±6, range 44–86, n=3 (n=3 at each agonist concentration); UTP (●), 67±3, range 56–79, n=3 (n=3–4). s.e. of each data point is $\leq 8\%$ of the normalized maximum response. The similar potency and effectiveness of ATP and UTP in these tissues suggests the presence of a $P_2$ receptor type sensitive to UTP on CF epithelium.

The foregoing is illustrative of the present invention, and not to be construed as limiting thereof. For example, those skilled in the art will appreciate that minor substitutions can be made to the active compounds described herein, without departing from the present invention. Accordingly, the invention is defined by the following claims, with equivalents of the claims included therein.

That which is claimed is:

1. A method of hydrating mucous secretions in the lungs of a subject in need of such treatment, comprising administering to the lungs of the subject a compound of Formula I below, or a pharmaceutically acceptable salt thereof, in an amount effective to hydrate lung mucous secretions:

wherein:
$X_1$, $X_2$, and $X_3$ are each independently selected from the group consisting of OH and SH;
$R_1$ is selected from the group consisting of O, imido, methylene, and dihalomethylene; and
$R_2$ is selected from the group consisting of H and Br.

2. A method according to claim 1, wherein said compound is delivered by administering an aerosol suspension of respirable particles comprised of said compound to the lungs of said subject.

3. A method according to claim 2, wherein said particles are selected from the group consisting of solid particles and liquid particles.

4. A method according to claim 2, wherein said aerosol is comprised of particles having a particle size within the range of about 1 to 10 microns.

5. A method according to claim 1, wherein said compound is administered in an amount sufficient to achieve concentrations thereof on the airway surfaces of said subject of from about $10^{-7}$ to about $10^{-3}$ Moles/liter.

6. A method according to claim 1, further comprising concurrently administering amiloride to said subject in an amount effective to inhibit the reabsorption of water from lung mucous secretions.

7. A method according to claim 1, wherein $X_2$ and $X_3$ are OH.

8. A method according to claim 1, wherein $R_1$ is oxygen.

9. A method according to claim 1, wherein $R_2$ is H.

10. A method according to claim 1, wherein said compound is selected from the group consisting of uridine 5'-triphosphate, uridine 5'-O-(3-thiotriphosphate), and the pharmaceutically acceptable salts thereof.

11. A method of treating cystic fibrosis in a human subject in need of such treatment, comprising administering by inhalation an aerosol suspension of respirable particles to the respiratory system of said subject, said particles comprised of a compound of Formula I below, or a pharmaceutically acceptable salt thereof:

wherein:
$X_1$, $X_2$, and $X_3$ are each independently selected from the group consisting of OH and SH;
$R_1$ is selected from the group consisting of O, imido, methylene, and dihalomethylene; and
$R_2$ is selected from the group consisting of H and Br;
in an amount effective to hydrate retained lung mucous secretions in the lungs of said subject, whereby the retained mucous secretions are more easily transported from the lungs via mucociliary action.

12. A method according to claim 11, wherein said particles are selected from the group consisting of solid particles and liquid particles.

13. A method according to claim 11, wherein said aerosol is comprised of particles having a particle size within the range of about 1 to 10 microns.

14. A method according to claim 11, wherein said compound is administered in an amount sufficient to achieve concentrations thereof on the airway surfaces of said subject of from about $10^{-7}$ to about $10^{-3}$ Moles/liter.

15. A method according to claim 11, further comprising concurrently administering amiloride to said subject in an amount effective to inhibit the reabsorption of water from lung mucous secretions.

16. A method according to claim 11, wherein $X_2$ and $X_3$ are OH.

17. A method according to claim 11, wherein $R_1$ is oxygen.

18. A method according to claim 11, wherein $R_2$ is H.

19. A method according to claim 1, wherein said compound is selected from the group consisting of uridine 5'-triphosphate, uridine 5'-O-(3-thiotriphosphate), and the pharmaceutically acceptable salts thereof.

20. A pharmaceutical formulation comprising amiloride in an amount effective to inhibit the reabsorption of water from lung mucus secretions and a compound of Formula I below, or a pharmaceutically acceptable salt thereof, in an aerosolizable form to be delivered to the lungs of a subject in an amount effective to hydrate lung mucous secretions, in a pharmaceutically acceptable carrier:

wherein:

$X_1$, $X_2$, and $X_3$ are each independently selected from the group consisting of OH and SH;

$R_1$ is selected from the group consisting of O, imido, methylene, and dihalomethylene; and $R_2$ is selected from the group consisting of H and Br.

21. A pharmaceutical formulation according to claim 20, wherein said carrier is selected from the group consisting of solid carriers and liquid carriers.

22. A pharmaceutical formulation according to claim 20, wherein $X_2$ and $X_3$ are OH.

23. A pharmaceutical formulation according to claim 20, wherein $R_1$ is oxygen.

24. A pharmaceutical formulation according to claim 20, wherein $R_2$ is H.

25. A pharmaceutical formulation according to claim 20, wherein said compound is selected from the group consisting of uridine 5'-triphosphate, uridine 5'-O-(3-thiotriphosphate), and the pharmaceutically acceptable salts thereof.

26. A composition according to claim 20, wherein said compound of Formula I is in the form of respirable particles ranging in size from 1 to 10 microns.

* * * * *

UNITED STATES PATENT AND TRADEMARK OFFICE
CERTIFICATE OF CORRECTION

PATENT NO.    : 5,292,498
DATED         : 08 March 1994
INVENTOR(S)   : Richard C. Boucher, Jr.

It is certified that error appears in the above-identified patent and that said Letters Patent is hereby corrected as shown below:

Column 1, Line 30, correct "Galacher" to read -- Gallacher --.

Column 3, Line 29, correct "$10^{-6}M$" to read -- $10^{-4}M$ --.

Column 5, Line 18 & 19, correct "$10^{317}$" to read -- $10^{-7}$ --.

Column 8, Line 63, correct "2MeSATp" to read -- 2MeSATP --.

Signed and Sealed this

Twenty-sixth Day of July, 1994

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,292,498
DATED : March 8, 1994
INVENTOR(S) : Richard C. Boucher, Jr.

It is certified that error appears in the above-identified patent and that said Letters Patent is hereby corrected as shown below:

At the following locations in the above-mentioned patent:
  SUMMARY OF THE INVENTION, column 2, line 10
  Claim 1, column 11, line 30
  Claim 11, column 12, line 15
  Claim 20, column 13, line 5
please replace the chemical structure that appears in all these locations as:

UNITED STATES PATENT AND TRADEMARK OFFICE
CERTIFICATE OF CORRECTION

PATENT NO. : 5,292,498
DATED : March 8, 1994
INVENTOR(S) : Richard C. Boucher, Jr.

Page 2 of 2

It is certified that error appears in the above-identified patent and that said Letters Patent is hereby corrected as shown below:

with the following structure:

Signed and Sealed this

Sixteenth Day of January, 2001

Attest:

Q. TODD DICKINSON

*Attesting Officer*        *Commissioner of Patents and Trademarks*